United States Patent [19]

Santhanam et al.

[11] Patent Number: 5,416,158
[45] Date of Patent: May 16, 1995

[54] CROSSLINKED CARBOXYLIC COPOLYMERS USEFUL AS RHEOLOGICAL ADDITIVES IN PERSONAL CARE AND PHARMACEUTICAL PRODUCTS

[75] Inventors: Mahalingham Santhanam, East Windsor; William W. Reichert, Freehold, both of N.J.

[73] Assignee: Rheox, Inc., Hightstown, N.J.

[21] Appl. No.: 202,623

[22] Filed: Feb. 28, 1994

Related U.S. Application Data

[63] Continuation of Ser. No. 57,855, May 7, 1993, abandoned, which is a continuation-in-part of Ser. No. 734,681, Jul. 23, 1991, abandoned, which is a continuation of Ser. No. 463,433, Jan. 11, 1990, abandoned.

[51] Int. Cl.$^6$ .................................................. C08K 5/04
[52] U.S. Cl. ..................................... 524/760; 524/773
[58] Field of Search ............... 524/317, 753, 773, 760; 424/70; 526/318.4, 318.44, 213

[56] References Cited

U.S. PATENT DOCUMENTS 3,931,085  1/1976  Drelich et al. ...................... 427/385

FOREIGN PATENT DOCUMENTS 2949843  7/1981  Germany .

Primary Examiner—Jeffrey T. Smith
Attorney, Agent, or Firm—Michael J. Cronin

[57] ABSTRACT

The invention relates to crosslinked carboxylic copolymers comprising an unsaturated carboxylic acid; a co-monomer containing a polymerizable ethylenically unsaturated group, a crosslinking monomer selected from the group consisting of triallylisocyanurate, triallyl trimellitate, and glyoxal bis(diallyl acetal) and an ethoxylated glyceride compound. The copolymer provides superior feel and appearance to a large variety of personal care and pharmaceutical products including cosmetics, creams, lotions and lipsticks.

7 Claims, No Drawings

CROSSLINKED CARBOXYLIC COPOLYMERS USEFUL AS RHEOLOGICAL ADDITIVES IN PERSONAL CARE AND PHARMACEUTICAL PRODUCTS

RELATED APPLICATION

This application is continuation of now abandoned U.S. patent application Ser. No. 08/057,855, filed Apr. 7, 1993, which was a continuation in part application of now abandoned U.S. patent application Ser. No. 07/734,681 filed Jul. 23, 1991, which application was a continuation of abandoned U.S. patent application Ser. No. 07/463,433 filed Jan. 11, 1990.

The present invention relates to carboxylic copolymers useful as rheological additives for personal care and pharmaceutical products.

BACKGROUND OF THE INVENTION

Materials that are capable of providing rheological properties including thickening to aqueous compositions find a variety of applications in cosmetic and pharmaceutical formulations, as well as other personal care products, in the form of creams, pastes, gels, ointments, and emulsions. Uses include hand creams, lipsticks, shampoos, hair conditioners and similar health and beauty aids. Such materials are also useful in textile printing inks, drilling muds, and aqueous coating compositions. Numerous rheological additives are currently employed throughout various industries, such as natural gums, for example, acacia, aliginate, carrageenan, guar, karaya, pectin, tragacanth, and xanthane; cellulose derivatives such as carboxymethyl cellulose, hydroxyethyl cellulose, and methyl hydroxypropyl cellulose; inorganic materials such as clays and fumed silica; and synthetic polymers such as acrylic acid based copolymers and polyoxypropylene/ethylene block polymers.

All of the prior art materials exhibit specific benefits and associated disadvantages for different aqueous systems. For example, two cellulose-derived substances that are widely employed are sodium carboxymethyl cellulose and nonionic hydroxyethyl cellulose. Both materials provide high thickening efficiency in water at low concentrations. However, these materials, and natural gums in general, are subject to biodegradation. Furthermore, although the cellulose derivatives provide excellent performance in terms of thickening, they do not impart to personal products in particular such features as superior feel and appearance that boost the consumer appeal for such products and provide customer satisfaction.

The use of synthetic polymers as rheological additives has become widespread throughout the health and personal care product marketplace due to their resistance to biodegradation and their ability to thicken personal care aqueous compositions with a smooth feel, smooth texture, and in certain instances, provide clear transparent gels. The most commonly employed synthetic polymers are lightly crosslinked carboxylic polymers prepared from unsaturated carboxylic acid containing monomers such as acrylic acid, methacrylic acid, and maleic anhydride. Some polymers of this type are described in U.S. Pat. No. 2,798,053. The high thickening efficiency of these polymers is achieved by crosslinking acrylic acid based polymers with a polyalkenyl polyether or polyhydric alcohol. The crosslinking renders the polymers water-swellable or water-dispersible.

Other known carboxylic polymers which maintain viscosities in aqueous solutions containing inorganic ions or salts are described in U.S. Pat. Nos. 3,915,921; 3,940,351; and 4,509,949. The copolymers consist of an unsaturated carboxylic acid monomer and one or more alkyl acrylate esters wherein the alkyl groups contain 10 to 30 carbon atoms and, optionally, a crosslinking monomer which is a polyfunctional vinylidene monomer containing at least two polymerizable $CH_2=C<$ groupings, the unsaturated bonds of the polymerizable groupings being non-conjugated with respect to each other.

Japanese Kokai 52-006789 discloses a water dispersible vinyl copolymer which is useful as a thickener in cosmetics and emulsions which is prepared by copolymerizing (meth)acrylic acid with triallylisocyanurate in the presence of a copolymerization catalyst.

U.S. Pat. No. 4,090,998, discloses crosslinked carboxyl-containing polymers which are water swellable in the form of their salts and are prepared by the polymerization of a monomeric mixture of maleic anhydride, indene, and a crosslinking monomer containing a plurality of $CH_2=C<$ groupings.

Processes for preparing the above described carboxylic polymers are described in U.S. Pat. Nos. 4,267,103 and 4,758,641.

U.S. Pat. No. 4,800,220 discloses crosslinked carboxylic copolymers for providing better resistance to viscosity losses in the presence of dissolved salts. Such copolymers are obtained by copolymerization of an unsaturated carboxylic monomer, a crosslinking agent, an acrylic or methacrylic ester with a polyalkylene glycol, and optionally, an alkyl acrylate or methacrylate.

U.S. Pat. Nos. 4,167,502; 4,138,381 and 4,230,844 disclose polymers of a polymerizable mixture which are useful as thickening and bodying agents when partially or completely neutralized in cosmetics, personal care products, latex paints, and oil well drilling compositions and which provide both good flow and leveling properties, as well as sag resistance to aqueous coating compositions.

U.S. Pat. No. 4,062,817 discloses carboxylic polymers comprising an unsaturated carboxylic acid, at least one alkyl acrylate or methacrylate ester in which the alkyl group contains 10 to 30 carbon atoms, and a second acrylate or methacrylate ester containing an alkyl group of from 1 to 9 carbon atoms, and optionally, a crosslinking monomer which is a polyfunctional vinylidene monomer containing at least two polymerizable $CH_2=C<$ groupings which rapidly absorb and retain large quantities of water and ionic fluids and are useful in disposable nonwoven articles. U.S. Pat. Nos. 4,668,731; 4,686,254; 4,778,737; 4,362,715; 3,953,591; and Canadian Pat. No. 1,067,411 describe the utilization of specific carboxylic copolymers as thickeners.

German patent DE 2,949,843 discloses a method for preparing carboxylic acid polymers in the presence of a polyvinyl pyrrolidinone polymer which acts as a protective colloid, said polymers being disclosed as useful as thickeners in the cosmetic and pharmaceutical fields. U.S. Pat. No. 3,931,085 teaches compositions useful for non-woven textile printing operations which comprise a synthetic resin, a water-soluble polymeric carboxylic thickener and a surfactant which is added to the synthetic resin composition without a crosslinker to create, enhance, or augment the triggering action which initiates the coagulation and precipitation of the synthetic resin. The patent discloses non-ionic surfactants which include ethoxylated compounds related to glycol esters of fatty acids. The use of certain ethoxylated surface-active agents in combination with specified carboxyl polymers is also shown in the art. See U.S. Pat. Nos. 4,375,533, 4,419,502 and 4,526,937.

The various carboxylic polymers described in the prior art are useful as thickeners for aqueous media and, in some cases, hydroalcoholic solvents. The maximum thickening ability of these polymers is attained upon neutralization of the carboxylic acid groups with a base such as ammonium hydroxide, sodium hydroxide, potassium hydroxide, or an amine. However, particularly in the field of cosmetic formulations, new thickeners are desired that are more efficient and are more easily dispersed, in combination with better feel and rub-up qualities, compared to prior art thickeners.

OBJECTS OF THE INVENTION

The present invention overcomes the problems and disadvantages of the prior art by providing crosslinked carboxylic copolymers that are useful as thickeners in aqueous systems and achieve better dispersibility, and non-tackiness and rub-up qualities compared to prior thickeners.

It is an object of the invention to provide a thickener for cosmetic use that provides superior "feel" and texture compared to prior art products.

It is a further object of the invention to provide an improved thickener which imparts superior feel and appearance to aqueous formulations such as creams, lotions and gels compared to prior art thickeners.

It is an additional object of the invention to provide an improved thickener which easily disperses in aqueous gel formulations compared to prior art thickeners.

Additional objects and advantages of the invention will be set forth in part in the description which follows, and in part will be obvious from the description, or may be learned by practice of the invention. The objects and advantages of the invention will be realized and attained by means of the instrumentalities and combinations, particularly pointed out in the appended claim.

SUMMARY OF THE INVENTION

The inventors have discovered that carboxylic copolymers containing a crosslinking monomer selected from the group consisting of triallylisocyanurate, triallyl trimellitate and glyoxal bis(diallyl acetal) in combination with an ethoxylated glyceride surfactant ester with an HLB value greater than 10 unexpectedly provide thickeners that have superior non-tackiness, feel and rub-up characteristics compared to prior art thickeners. The ethoxylated glyceride employed in the present invention is prepared by the ethoxylation of an acyl glyceride, e.g., ethoxylation of a monoglyceride. The surfactant ester, which has a high affinity for the polymer, is added to a non-hydrogen bonding solvent for the polymerization reaction in which it is not soluble. The monomers which comprise the polymer are soluble in the polymerization solvent. As the polymer is formed, the polymer precipitates and the surfactant ester is adsorbed on the surface of the polymer.

The thickeners disclosed in the present invention not only provide an increase in viscosity but also provide superior emulsion stability so that the product displays self stability and does not separate, and remains acceptable in terms of homogeneity and aesthetic qualities to the ultimate consumer. Additionally, the thickeners also impart superior "feel" (non-tackiness) and appearance to aqueous formulations in the form of personal care (cosmetic) products.

To achieve the objects and in accordance with the purpose of the invention, as embodied and broadly described herein, the invention provides crosslinked carboxylic copolymers that comprise (a) an unsaturated carboxylic acid; (b) an additional comonomer containing a polymerizable ethylenically unsaturated group; (c) a crosslinking monomer selected from the group consisting of triallylisocyanurate, triallyl trimellitate, and glyoxal bis(diallyl acetal); and (d) an ethoxylated glyceride compound of the formula

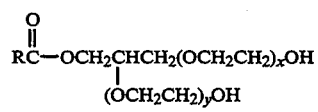

wherein R represents an alkyl group of from $C_8$ to $C18$ and the sum of $x+y$ is from 20 to 300. Since the carboxylic copolymers of the invention are not intended for use in salt or ionic environments and the presence of acrylic acid and methacrylic acid esters would subtract from the performance of the carboxylic copolymers of the invention, the additional comonomer containing a polymerizable ethylenically unsaturated group is not to be selected from the group consisting of alkyl acrylates, alkyl methacrylates, acrylic acid esters derived from a polyalkylene glycol and methacrylic acid esters derived from a polyalkylene glycol.

The compositions of the invention are alkali swellable and lightly cross linked and are useful as thickeners and stabilizers, particularly for cosmetic formulations, including gels, creams and lotions, for personal care products, textile printing inks and pastes, paints, drilling muds, textile sizings, pharmaceuticals, papermaking, oil recovery and food processing. Further, aqueous gels containing the crosslinked carboxylic copolymers of the invention, in combination with an ethoxylated glyceride, have improved clarity.

DESCRIPTION OF THE PREFERRED EMBODIMENTS

Reference will now be made in detail to the preferred embodiments of the invention.

The carboxylic copolymers of the invention may be prepared by copolymerizing (a) from about 70% to about 99%, more preferably from about 92% to about 95% by weight of at least one unsaturated carboxylic monomer; (b) from about 2 to about 29%, more preferably from about 2% to about 15% by weight of a monomer containing a polymerizable ethylenically unsaturated group, wherein said group is not selected from the group consisting of alkyl acrylates, alkyl methacrylates, acrylic acid esters derived from a polyalkylene glycol and methacrylic acid esters derived from a polyalkylene glycol; (c) from about 0.8% to about 1.2%, more preferably from about 0.9% to about 1.1% by weight of at least one crosslinking monomer selected from the group consisting of triallylisocyanurate, triallyl trimellitate, and glyoxal bis(diallyl acetal); and (d) from about 0.1 to about 1.0%, preferably from about 0.5% to about 0.75% by weight of an ethoxylated glyceride of the formula

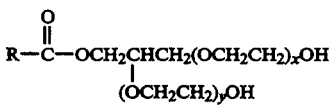

wherein R represents an alkyl group of from $C_8$ to $C_{18}$ and the sum of $x+y$ is from 20 to 300.

Most preferably, the carboxylic copolymers of the invention are prepared by copolymerizing (a) about 92% by weight of at least one unsaturated carboxylic monomer; (b) from about 6% to about 7% by weight of a monomer containing a polymerizable ethylenically unsaturated group; (c) about 1% by weight of at least one crosslinking agent selected from the group consisting of triallylisocyanurate, triallyl trimellitate, and glyoxal bis(diallyl acetal); and (d) about 0.5% by weight of an ethoxylated glyceride of the type described in the formula above.

The unsaturated carboxylic monomers employed in the invention are preferably olefinically unsaturated carboxylic acids containing at least one activated carbon-carbon double bond and at least one carboxylic acid group wherein the olefinic double bond is present in the carboxylic acid monomer in either an alpha, beta position relative to the carboxyl group or in the form of a methylene end group such as $CH_2=C<$. Exemplary suitable olefinically unsaturated carboxylic acids include acrylic acid, methacrylic acid, ethacrylic acid, fumaric acid, crotonic acid, itaconic acid, styrylacrylic acid, glutaconic acid, maleic acid and acid anhydrides such as maleic anhydride. Preferably, acrylic acid or methacrylic acid are employed: most preferably acrylic acid is employed.

Monomers which contain a polymerizable ethylenically unsaturated group are also employed in the copolymers of the invention, providing that the monomers do not adversely effect the thickening properties of the crosslinked carboxylic monomers. Exemplary suitable copolymerizable monomers contain at least one terminal $CH_2=C<$ group and may include vinyl acetate, vinyl pyrrolidinone, methyl vinyl ether, ethyl vinyl ether, acrylamide, methacrylamide, and methyl vinyl ketone.

The crosslinking monomers for use in the invention include triallylisocyanurate, triallyl trimellitate and glyoxal bis(diallyl acetal) which is also known as tetraallyloxyethane. Most preferably, triallylisocyanurate is employed.

Glycerides suitable for use in the present invention include ethoxylated glycerides derived from the ethoxylation of a monoglyceride (for example, PEG-20 glyceryl oleate is obtained by the ethoxylation of glycerol [mono]oleate which contains two -OH groups each of which may react with ethylene oxide until the total level of ethylene oxide or EO equals 20 units). Exemplary suitable ethoxylated glycerides include PEG-30 glyceryl monococoate (commercially available as Varonic LI-63 from Sherex Chemical Company, Inc.), PEG 83 glyceryl monotallowate (commercially available as Varonic LI-48 from Sherex Chemical Company, Inc.), PEG 300 glyceryl monotallowate (commercially available as Varonic LI-420 from Sherex Chemical Company, Inc.), and PEG 30 glyceryl monotallowate (commercially available as Varonic LI-42 from Sherex Chemical Company, Inc.).

Polymerization of the monomers to prepare the crosslinked carboxylic copolymers of the present invention is preferably carried out in a solvent in the presence of a free radical catalyst in an inert atmosphere in a closed reaction vessel equipped with a stirrer under autogenous pressure, artificially induced pressure, or in an open vessel equipped with a stirrer under an inert atmosphere or under reflux at atmospheric pressure. The polymerization temperature is preferably between from about 0° C. to about 150° C., more preferably from about 25° C. to about 100° C. The reaction can be conducted either batchwise or with the continuous addition of reactants.

Preferred radical catalysts for initiating the polymerization reaction include peroxide and hydroperoxide compounds such as benzoyl peroxide, lauroyl peroxide, caprylyl peroxide, tert-butyl peroxide, tert-butyl hydroperoxide; perbenzoates such as t-butyl perbenzoate, peroxyesters such as 2,5-dimethyl-2,5-bis(2-ethyl hexoylperoxy)hexane; and azo compounds such as azobis-(isobutyronitrile) and azobis(isovaleronitrile). The initiators may be employed separately or in a mixture. The free radical generating initiator is preferably employed in an amount of from about 0.2% to about 1.2% by weight of the total monomers, more preferably from about 0.25% to about 0.75% by weight of the total monomer content, most preferably from about 0.3% to about 0.6% by weight of the total monomer content.

The polymerization reaction may be carried out in an organic solvent in which the monomers are soluble, but in which the polymers of this invention are insoluble. Consequently, the polymer precipitates out of the polymerization solvent in the form of fine particles. The solvent is then removed via filtration methods and the polymer is dried. The solvent employed must be inert to the monomers, the polymers, and the ethoxylated surfactant. Exemplary suitable solvents include aliphatic, cycloaliphatic, aromatic, halogen-substituted hydrocarbons, and alkyl-aromatic solvents such as hexane, heptane, octane, cyclohexane, benzene, toluene, xylene, chlorobenzene, carbon tetrachloride, trichloroethylene, and trichloroethane. Preferably, hexane, heptane, or cyclohexane is employed. Most preferably, cyclohexane is employed. The concentration of the monomers in the polymerization solvent is preferably from about 5% to 25%, more preferably from about 10% to about 25% by weight. The inventors have found that at higher concentrations, the polymerization reaction is strongly exothermic and too viscous.

The ethoxylated surfactant should be insoluble (incompatible) with the polymerization solvent. Preferably, the glyceride used has an HLB value greater than 10, more preferably, from about 11 to about 20.

The crosslinked carboxylic polymers of the invention enhance the appearance and performance of gel, cream and lotion formulations through improved thickening, improved emulsion stability, and elegant feel. When the crosslinked carboxylic copolymers are added to an aqueous system, thickening is obtained at a pH of from about 2 to about 3, but is greatly increased when the carboxylic acid groups in the polymer are neutralized, the optimum pH being between about 6 and about 9. Exemplary suitable neutralizing agents for use in the invention include aqueous ammonia, sodium hydroxide, potassium hydroxide, sodium carbonate, and amines such as monoethanolamine, diethanolamine, triethanolamine, monoethylamine, and the like. Through the use of primary, secondary, or tertiary organic amines, it is possible to thicken hydroalcoholic media with the crosslinked carboxyl polymers of the present invention.

The crosslinked carboxylic copolymers of the invention are particularly effective in enhancing the appearance and performance of cream and lotion formulations through elegant feel. The crosslinked carboxylic copolymers of the present invention are effective in thickening aqueous media from about 0.1% by weight of the total weight of the medium to be thickened. The copolymers of the invention are generally employed in an amount of from about 0.1% to about 1.0% by weight of the total weight of the medium to be thickened.

The high molecular weight, lightly crosslinked polymers of the invention likely function rheologically by forming a three-dimensional microgel structure following dispersion in water and neutralization with an appropriate base. The resulting microgel network serves to suspend dispersed particles or oil droplets while displaying shear-thinning flow behavior.

The thickening and emulsion stabilizing mechanism associated with the lightly crosslinked composition including the glyceride surfactant is directly related to its unique chemical composition and structure. Due to the presence of the particular composition, the polymers are insoluble in water, but capable of swelling rapidly in it when neutralized with a base. In the unneutralized, unsolvated state, the polymer chains exist in coiled form and display only limited thickening capabilities. When dispersed in water, the polymer uncoils to some extent and thickens the medium. However, to achieve a dramatic increase in viscosity, the polymer chains need to be uncoiled to the maximum extent. This in effect is achieved with the complete neutralization of the acid functionalities and by use of the glyceride surfactant. The presence of the negatively charged carboxylate groups in close proximity to each other leads to a charge repulsion which causes the polymer chains to occupy a maximum volume as they uncoil to an extended structure. This expansion leads to a dramatic increase in viscosity of the aqueous medium due to the entanglement of the long thread-like ends of the crosslinked polymers. Consequently, low concentrations of polymers which have been crosslinked with a very small amount of the specific crosslinkers disclosed, in combination with the alkoxylated glyceride surfactant, are able to thicken aqueous systems in an efficient manner not previously achieved.

The highly efficient thickening mechanism associated with the inventive polymers is not due solely to polymer chain entangelement, but also occurs due to the presence of non-interactive microgel particles which swell dramatically to give rise to highly viscous solutions and gels. Consequently, the influence of the presence of the specified crosslinkers disclosed herein and their associated functionality in combination with the glyceride surfactant changes the thickening mechanism of previously known lightly crosslinked carboxyl polymers to directly achieve modern cosmetic aesthetic properties, such as elegant feel and smoothness, providing enhanced aesthetic and psychological satisfaction to a consumer.

The invention will be further clarified by the following examples, which are intended to be exemplary of the development.

EXAMPLE 1

500 ml of cyclohexane was charged into a 1-liter resin kettle equipped with a thermometer, condenser, two addition funnels, nitrogen inlet tube and mechanical stirrer. The solvent was heated to reflux (80°–81° C.) under nitrogen. 46 g acrylic acid, 3.5 g vinyl acetate, 0.5 g triallylisocyanurate and 0.25 g Varonic LI-63 (PEG 30 glyceryl monococoate commercially available from Sherex Chemical Company, Inc.) were combined in a separate vessel and stirred until a homogeneous mixture was obtained. The homogeneous monomer mixture was placed in an addition funnel. 0.25 g of benzoyl peroxide was added to 10 ml cyclohexane and heated slowly with stirring to 70° C. until dissolved. The heated initiator solution was transferred to a heated addition funnel. The heated initiator solution and the monomer mixture were added simultaneously over a period of 30 minutes to the reactor containing cyclohexane under reflux. The reaction mixture was then maintained at reflux (80°–81° C.) for 4 hours and then allowed to cool. The white precipitate which formed during the reaction was filtered, washed with 50 ml of cyclohexane, and the resulting wet polymer cake was dried under vacuum at 80° C. for 16 hours.

Samples of the polymer were added to deionized water at concentrations of 0.5% by weight. The solution was stirred at 600 rpm for 30 minutes to disperse the polymer completely.

At this time, the dispersibility of the polymer in a 400 ml beaker was visually determined on a scale of 1 to 6 as follows:
1. no particles
2. 0–5 particles
3. 6–10 particles
4. 10–20 particles
5. >20 particles
6. polymer did not disperse The polymer solutions were then neutralized with triethanolamine to a pH of 7. The solutions were stirred for an additional 20 minutes and then measured for viscosity and clarity. The viscosity of this solution was measured with a Brookfield RVT viscometer at 20 rpm equipped with a #6 spindle in accordance with ASTM D2196-81. The gel clarities were judged on a scale of from clear, slightly hazy, hazy, and opaque.

The viscosities of the gels prepared at 0.5% polymer concentrations and physical appearances are set forth in Table 1.

EXAMPLE 2

500 ml of cyclohexane was charged into a 1-liter resin kettle equipped with a thermometer, condenser, two addition funnels, nitrogen inlet tube and mechanical stirrer. The cyclohexane was heated to 70° C. under nitrogen. 0.5 g of triallyl isocyanurate and 3.5 g of vinyl acetate were added to the kettle. 0.1 g of benzoyl peroxide was dissolved in 1.0 ml methyl ethyl ketone and 1.0 ml cyclohexane. The mixture was added to the reactor over a period of 15 minutes via a syringe pump. After addition was completed, the reaction mixture was slowly heated to reflux (80°–81° C). 46 g of acrylic acid and 0.13 g Varonic LI-63 were placed in an addition funnel and another portion of the initiator solution (0.25 g of benzoyl peroxide dissolved in 1.5 ml methyl ethyl ketone and 1.5 ml cyclohexane) was placed in a syringe pump. The two materials were added simultaneously over a period of 30 minutes and the reaction was allowed to proceed for 4 hours at reflux and then the reactor contents were allowed to cool to room temperature. The white precipitate which formed during the reaction was filtered through a Buchner funnel and dried under vacuum at room temperature for 16 hours. Samples of the polymer were prepared as 0.5% polymer gels and evaluated in accordance with the procedures set forth in Example 1. The results are set forth in Table 1.

COMPARATIVE EXAMPLE A 500 ml of cyclohexane were charged into a 1-liter resin kettle equipped with a thermometer, condenser, two addition funnels, nitrogen inlet tube and mechanical stirrer. The solvent was heated to reflux (80°–81° C.) under nitrogen. 46 g acrylic acid, 3.5 g vinyl acetate, and 0.5 g triallylisocyanurate were combined in a separate vessel and stirred until a homogeneous mixture was obtained. This homogeneous monomer mixture was placed in an addition funnel. 0.25 g of benzoyl peroxide was added to 10 ml cyclohexane and heated slowly with stirring to 70° C. until dissolved. This heated initiator solution and the monomer mixture were added simultaneously over a period of 30 minutes to the reactor containing cyclohexane under reflux. The reaction mixture was then maintained at reflux for 4 hours and then allowed to cool. The white precipitate which formed during the reaction was filtered, washed with 50 ml of cyclohexane and the resulting wet polymer cake was dried under vacuum at 80° C. for 16 hours. Samples of the polymer were prepared as 0.5% polymer gels and evaluated in accordance with the procedures set forth in Example 1. The results are set forth in Table 1.

TABLE 1

| THICKENING EFFICIENCY IN AQUEOUS GELS NEUTRALIZED WITH TRIETHANOLAMINE | | | |
|---|---|---|---|
| Example | Brookfield Viscosity 20 rpm (cP) 0.5% Concentration | Appearance | Disp. |
| 1 | 37,000 | very sl. hazy | 2 |
| 2 | 42,000 | sl. hazy | 1 |
| Comp. Ex. A | 36,250 | very hazy | 3 |

The above examples describe the polymerization of acrylic acid, vinyl acetate, and traillyl isocyanurate in a cyclohexane solvent. Benzoyl peroxide has been used as an initiator (or free radical catalyst) for the polymerization. The polymerization is conducted in the presence of an ethoxylated glyceride. The ethoxylated glyceride is not soluble (or miscible) in the polymerization solvent and is believed to be adsorbed onto the polymer surface through a hydrophilic bonding mechanism. The results in Table 1 clearly demonstrate that the presence of the ethoxylated glyceride on the surface of the polymer surprisingly enhances the feel and emulsion properties associated with the carboxylic acid vinyl acetate copolymers when incorporated as thickeners for personal care products.

The copolymers of the invention can be widely used in such personal care products due to their ability to thicken aqueous-based formulations and also stabilize oil-in-water emulsions. These additives because of their composition impart shear thinning as well as desired aesthetic properties such as elegant feel and non-tackiness. Many commercial factors will influence the use of these rheological additives and, consequently, the aesthetic properties of gels prepared with such copolymers.

Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A rheological additive comprising:
   i) a copolymer formed from reactants comprising:
      (a) an unsaturated carboxylic acid in an amount of 70–99% by weight;
      (b) a monomer containing a polymerizable ethylenically unsaturated group in an amount of 0.2 to 29% by weight wherein said monomer is not selected from the group consisting of indene, alkyl acrylates, alkyl methacrylates, acrylic acid esters derived from a polyalkylene glycol and methacrylic acid esters derived from a polyalkylene glycol, and
      (c) at least one crosslinking monomer selected from the group consisting of triallylisocyanurate, triallyl trimellitate, and glyoxal bis(diallyl acetal) in an amount of 0.8–1.0% by weight, and
   ii) an ethoxylated glyceride compound adsorbed on the surface of the copolymer.

2. The rheological additive of claim 1 wherein the ethoxylated glyceride compound is of the formula:

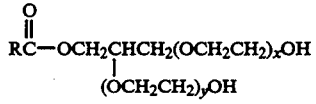

wherein R represents an alkyl group of from $C_8$ to $C_{18}$ and the sum of $x+y$ is from 20 to 300.

3. The rheological additive of claim 1 wherein said unsaturated carboxylic acid is an olefinically unsaturated acid.

4. The rheological additive of claim 2 wherein said olefinically unsaturated acid is selected from the group consisting of acrylic acid, methacrylic acid, ethacrylic acid, fumaric acid, crotonic acid, itaconic acid, styrylacrylic acid, glutaconic acid, and maleic acid.

5. The rheological additive of claim 1 wherein said crosslinking monomer is triallylisocyanurate.

6. The rheological additive of claim 1 wherein said monomer containing a polymerized ethylenically unsaturated group is at least one selected from the group consisting of vinyl acetate, vinyl pyrrolidinone, methyl vinyl ether, ethyl vinyl ether, acrylamide, methacrylamide and methyl vinyl ketone.

7. The rheological additive of claim 1 wherein the rheological additive has a pH of from about 6 to about 9.

* * * * *